United States Patent
Cuzzato et al.

(10) Patent No.: US 6,232,514 B1
(45) Date of Patent: *May 15, 2001

(54) PROCESS FOR PREPARING PENTAFLUOROETHANE

(75) Inventors: Paolo Cuzzato, Treviso; Antonio Masiero, Stanghella; Francesco Rinaldi, Padua, all of (IT)

(73) Assignee: Ausimont S.p.A. (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/812,311

(22) Filed: Mar. 5, 1997

Related U.S. Application Data

(63) Continuation of application No. 08/566,450, filed on Dec. 1, 1995, now abandoned, which is a continuation of application No. 08/288,224, filed on Aug. 9, 1994, now abandoned.

(30) Foreign Application Priority Data

Aug. 13, 1993 (IT) .............................. MI93A1828

(51) Int. Cl.$^7$ ................................................... C07C 17/00
(52) U.S. Cl. .......................................... 570/169; 570/166
(58) Field of Search ..................... 570/169, 166

(56) References Cited

U.S. PATENT DOCUMENTS

| | | |
|---|---|---|
| 3,258,500 | 6/1966 | Swamer et al. . |
| 3,755,477 | 8/1973 | Firth et al. . |
| 4,766,620 | 8/1988 | Boyhan . |
| 4,843,181 * | 6/1989 | Gumprecht .......................... 570/169 |
| 4,967,023 * | 10/1990 | Carmello et al. .................... 570/169 |
| 5,334,787 * | 8/1994 | Felix et al. .......................... 570/169 |

FOREIGN PATENT DOCUMENTS

| | | |
|---|---|---|
| 0 349 298 | 1/1990 | (EP) . |
| 0 408 005 | 1/1991 | (EP) . |
| 0 513 823 | 11/1992 | (EP) . |

* cited by examiner

*Primary Examiner*—Alan Siegel
(74) *Attorney, Agent, or Firm*—Finnegan, Henderson, Farabow, Garrett & Dunner, L.L.P.

(57) ABSTRACT

Process for preparing pentafluoroethane (HFC-125) wherein 1,1,1-trifluorodichloroethane (HFC-123) is reacted with HF at a temperature from 310° to 380° C., in the presence of a catalyst comprising $Cr_2O_3$ supported on preformed $AlF_3$. HFC-125 is obtained with high yields (up to 60–70% and over), high conversions (over 80%) and high selectivity, i.e. formation of by-product in very low amounts (5% by moles at most) Moreover, the catalyst maintains a high activity for a long time also with high organic charges.

9 Claims, No Drawings

PROCESS FOR PREPARING PENTAFLUOROETHANE

This application is a continuation of application Ser. No. 08/566,450, filed Dec. 1, 1996, now abandoned; which is a continuation of application Ser. No. 08/288,224, filed Aug. 9, 1994 now abandoned.

The present invention relates to a process for preparing pentafluoroethane (HFC-125). More particularly, the present invention relates to a process for preparing HFC-125 by catalytic fluorination with HF of 1,1,1-trifluorodichloroethane (HCFC-123).

It is known that HFC-125, since it does not contain chlorine, has no destructive potential towards the atmospheric ozone and therefore it is an excellent substitute of the conventional chlorofluorocarbons (CFC), which, as known, will be subjected within a few years to severe restrictions both for the production and for the use, according to what provided for by the Montreal Protocol. It is therefore evident the utility of disposing of a process for the manufacture of HFC-125 on industrial scale.

Fluorination processes of tetrachloroethylene with HF in the presence of a catalyst based on an oxide of a transition metal, such as chromium, nickel, cobalt, manganese, etc. (see for isntance U.S. Pat. Nos. 3,258,500, 3,755,477 and 4,766,260), are known in the art. Such processes lead to the achievement of mixtures of more or less fluorinated saturated products, among which 1,1,1-trifluorodichloroethane (HCFC-123), 1,1,1,2-tetra-fluorochloroethane (HCFC-124) and HFC-125. An inconvenience common to such processes is the poor selectivity obtainable in the reactions conditions necessary for producing HFC-125 with satisfactory yields: as a matter of fact, remarkable unrecoverable fractions of disproportionation by-products form, such as CFC-113 ($CCl_2F$—$CClF_2$) and CFC-114 ($CClF_2$—$CClF_2$). There is also the formation of chloroolefinic by-products, in particular CFC-1112 (CFCl=CFCl) and CFC-1112a ($CF_2$=$CCl_2$), which, as known, cause problems of toxicity and chemical stability, whereby they must be successively removed. If one tries to optimize the conditions (for instance by falling the reaction temperature) so as to increase the selectivity, the production of HFC-125 decreases unacceptably for an application on industrial scale. Moreover, such processes have the great inceonvenience of a quick decay of the catalytic activity after 70–90 hours of maximum reaction, activity which, even after regeneration of the catalyst, according to known techniques, cannot be restored to the initial values. They are therefore unsuitable processes for continuous productions on industrial scale.

The same problems of decay of the catalytic activity were found by the Applicant for the process described in the patent application EP 349,298, wherein HCFC-123 and/or HCFC-124 are prepared by fluorination of pentahaloethane of formula $C_2HX_{5-n}F_n$, where X=Cl, Br, n=0.3, with HF at 250°–450° C., in the presence of a catalyst formed by a metal at oxidation state>0, selected from Cr, Mn, Ni, Rh, Co, supported on a compound essentially formed by Al and F, in ratios corresponding to a content of $AlF_3 \geq 90\%$ by weight. Such a catalyst is prepared according to the following scheme:
(a) soaking of $Al_2O_3$ in an aqueous solution of a metal salt;
(b) drying at 100° C. for 18 hours and subsequent treatment with $N_2$ at 400° C. to remove any moisture trace;
(c) fluorination with HF, diluted with $N_2$, at 450° C., so as to obtain a content in fluorine corresponding to an amount of $AlF_3$ higher than 90% by weight.
Preferred metals are Ni, Mn and Co.

According to what reported in the above mentioned patent application EP-349,298, the reaction of HCFC-123 with HF leads to the formation of HCFC-124 with good yields, while HFC-125 is present in the final mixture in small amaounts: 7.5% by weight at most with a reaction temperature of 400° C., while operating at 350° C., only 0.5% by weight of HFC-125 is obtained. They are quite unsatisfactory yields for a production of HFC-125 on industrial scale. From such data, it is evident that it is necessary to work at temperatures higher than 400° C., in order to obtain sufficiently high yields in HFC-125. As explained above, this would unavoidably involve the formation of considerable amounts of by-products.

The Applicant has now surprisingly found that by carrying out the fluorination of the HCFC-123 with HF on a catalyst formed by $Cr_2O_3$ supported on preformed $AlF_3$ (i.e. $AlF_3$ prepared before the addition of the metal catalyst), at a temperature comprised between 310° and 380° C., HFC-125 with high yields (up to 60–70% and over), high conversions (over 80%) and high selectivity, i.e. formation of by-products in very low amounts (50% by moles at most), is obtained. In particular, the chloroolefinic by-products are present in slight amounts, generally lower than 0.05% by moles. Moreover, the catalyst maintains an high activity for a long time even with high organic charges, and can be easily regenerated, for instance with air at high temperature (350°–500° C.).

Object of the present invention is therefore a process for preparing pentafluoroethane (HFC-125), which comprises reacting 1,1,1-trifluorodichloroethane (HCFC-123) with HF at a temperature comprised from 310° to 380° C., preferably from 320° to 350° C., in the presence of a catalyst comprising $Cr_2O_3$ supported an preformed $AlF_3$.

The catalyst used in the process object of the present invention can be prepared according to the following method: (a) soaking of $AlF_3$ in an aqueous solution of a soluble Cr (III) salt (for instance $CrCl_3.6H_2O$); (b) drying, for instance, by air heating at 100–120° C.; (c) activation of the catalyst by air or nitrogen at 200–600° C., preferably from 350° to 500° C., optionally in the presence of steam.

The amount of $Cr_2O_3$ is generally comprised from 1 to 15% by weight, calculated as Cr amount with respect to the total weight-of the catalyst.

The support of $AlF_3$ can be in the form of powder having the particles diameter generally comprised from 20 to 200 μm, or of pellets. Supports with high surface area, of 25–30 $m^2/g$ order, are generalay preferred.

The process object of the present invention can be carried out in fixed bed or, preferably, fluid bed reactors.

The HFC-125 can be easily recovered from the mixture flowing out from the reactor by fractional distillation according to known techniques.

The molar ratio between fed HF and HCFC-123 is not a critical parameter and is generally comprised between 1/1 and 10/1, preferably between 1.5/1 and 5/1. The contact times, measured as ratio between the reactants flow in the reaction conditions and the volume of the catalytic bed in rest conditions, are generally comprised from 1 to 20 sec, preferably from 1.5 and 10 sec. The pressure is not a critical parameter: pressures around the atmospheric one or higher pressures are generally used.

The following examples are given for illustrative purposes and not limitative of the scope of the invention itself.

EXAMPLE 1

Preparation of the Catalyst 240 g of $AlF_3$ in powder (with particles having a diameter comprised from 20 to 200 μn) were soaked in a solution prepared by dissolving 118 g of $CrCl_3.6H_2O$ in distilled water until a total volume of about 105 ml. The soaking was carried out by dripping the solution into the $AlF_3$ under stirring, subdividing such a solution in three equal parts; when the dripping of each part was over, the catalyst was partially dried in stove at 110° C. for 1.5 hours. The so obtained catalyst was then loaded into a tubular Inconel® 600 reactor having an inner diameter of 5 cm, an height of 80 cm and equipped at the base with a sintered Inconel® porous separator, in order to evenly distribute the gas entering from the bottom and to support the rest catalytic bed. A sheat was placed in the middle of the reactor, wherein the thermocouples were put for temperature measurements. The so loaded reactor was heated up to 400° C. in nitrogen flow at 100 Nl/hour and kept at such a temperature for 10 hours.

Fluorination of the HCFC-123

440 g (330 ml) of the so prepared catalyst were put in the above described tubular Inconel® reactor. By keeping the pressure at a value slightly higher than the atmospheric one and the temperature at 350° C., HCFC-123 with a flow of 0.49 moles/hour and anhydrous HF with a flow of 1.95 moles/hour were fed, achieving a ratio HF/123 equal to 4 and a contact time of 9.5 sec. The reaction was carried out for 120 hours without noticing any decay in the catalyst activity. The gas flowing out from the reactor were washed in water to adsorb the acidity, dried, condensed and analyzed by gas-liquid gaschromatograph. The results are reported in Table 1. The conversion of the HCFC-123 is equal to 84%, the selectivity in HFC-125/HCFC-124 is 94%. The by-products are formed by chlorofluorocarbons having 2 carbon atoms. In Table 1 the CFC-1112/1112a ratio present in the by-products is also indicated.

EXAMPLE 2

Example 1 was repeated according to the same modalities above described. The reaction conditions and the mixture composition flowing out from the reactor are reported in Table 1, where the HCFC-123a (1,1,2-trifluoro-1,2-dichloroethane) ratio present in the HCFC-123 at the beginning of the reaction and when the reaction is over is also indicated (the ratio is referred to the total amount of HCFC-123 and 123a). It is a particularly undesired by-product, since it tends to decompose forming HCl, an highly corrosive product. It can be noticed how the process object of the present invention leads to a meaningful reduction of the amount of HCFC-123a present in the mixture.

TABLE 1

| EX. | REACTANTS (moles/hour) | | MOLAR RATIO | TEMP. | CONTACT TIME | OUTFLOWING MIXTURE COMPOSITION (% moles) | | | |
|---|---|---|---|---|---|---|---|---|---|
| | HF | 123 | HF/123 | (° C.) | (sec) | 125 | 124 | 123 | others |
| 1 | 1.95 | 0.49 | 4 | 350 | 9.5 | 61.4 | 17.9 | 15.7 | 5.0 (0.03%)* |
| 2 | 3.0 | 0.6 (4.4%)** | 5 | 320 | 5 | 23.6 | 31.3 | 43.4 (<1%)** | 1.7 (0.05%)* |

*CFC-1112/1112a
**HCFC-123a

What is claimed is:

1. Process for preparing pentafluoroethane (HFC-125) with a conversion of over 80%, comprising:
    preparing a catalyst consisting essentially of $Cr_2O_3$ supported on preformed $AlF_3$ by soaking $AlF_3$ in an aqueous solution of a soluble Cr (III) salt, drying said soaked $AlF_3$, and activating the catalyst in air or nitrogen at 200–600° C. so that the catalyst has catalytic activity; and
    reacting 1,1,1-trifluorodichloroethane (HCFC-123) with HF at a temperature from 310° to 380° C. in the presence of said catalyst and with a contact time of from 1 to 10 seconds.

2. Process according to claim 1, wherein the reaction temperature is from 320° to 350°.

3. Process according to claim 1 or claim 2, wherein the molar ratio between fed HF and HCFC-123 is between 1/1 and 10/1.

4. Process according to claim 1 or claim 2, wherein the amount of $Cr_2O_3$ present in the catalyst is between 1 and 15% by weight, calculated as Cr amount with respect to the total weight of the catalyst.

5. Process according to claim 1 or claim 2, wherein said process is carried out in a fluid bed reactor.

6. Process of claim 1, wherein said catalyst is activated in the presence of steam.

7. Process of claim 1, wherein said catalyst maintains its catalytic activity for 90 hours of reaction time.

8. Process of claim 7, wherein said catalyst maintains its catalytic activity for 120 hours of reaction time.

9. Process of claim 1, further comprising regenerating said catalyst's catalytic activity in air at a temperature of 350° to 500° C.

* * * * *